(12) United States Patent
Wang et al.

(10) Patent No.: US 7,728,979 B2
(45) Date of Patent: Jun. 1, 2010

(54) METHOD AND DEVICE FOR CHARACTERIZING ANALYTE USING ELECTRO-OPTICALLY MODULATED SURFACE PLASMON RESONANCE BASED ON PHASE DETECTION

(75) Inventors: Tzyy-Jiann Wang, Taipei (TW); Chih-Wuei Hsieh, Taipei (TW)

(73) Assignee: National Taipei University Technology, Taipei (TW)

( * ) Notice: Subject to any disclaimer, the term of this patent is extended or adjusted under 35 U.S.C. 154(b) by 442 days.

(21) Appl. No.: 11/749,142

(22) Filed: May 15, 2007

(65) Prior Publication Data
US 2008/0285033 A1    Nov. 20, 2008

(51) Int. Cl.
*G01N 21/55* (2006.01)
(52) U.S. Cl. ...................................... 356/445
(58) Field of Classification Search ................ None
See application file for complete search history.

(56) References Cited

U.S. PATENT DOCUMENTS 7,298,488 B2 *  11/2007  Wang et al. ................. 356/445

* cited by examiner

*Primary Examiner*—Gregory J Toatley, Jr.
*Assistant Examiner*—Amanda H Merlino
(74) *Attorney, Agent, or Firm*—Chun-Ming Shih

(57) ABSTRACT

A method and a device for detecting object properties using electro-optically modulated surface plasmon resonance (SPR) based on phase detection is disclosed. In the case of a surface plasmon resonance sensing device according to the present invention, the voltage is applied on the sensing device made of an electro-optic material to modulate the surface plasmon resonance condition by varying the wavevector of the incident lightwave. The relation between the phase of output optical wave and the applied voltage is measured, and the solution concentration or the material property is obtained by using the slope of a regression straight line of this relations. The invention can be used in the experimental arrangements of the attenuated-total-reflection (ATR) structure and the optical waveguide structure, and has advantages of high sensitivity, high stability, small bulk, low equipment cost, etc.

15 Claims, 6 Drawing Sheets

METHOD AND DEVICE FOR CHARACTERIZING ANALYTE USING ELECTRO-OPTICALLY MODULATED SURFACE PLASMON RESONANCE BASED ON PHASE DETECTION

BACKGROUND OF THE INVENTION

The present invention provides a technology of electro-optically modulated surface plasmon resonance (SPR) based on phase detection, which can be utilized to sense material characteristics, concentration of biochemical matter, and interaction intensity of biochemical molecules. Moreover, design and manufacture of sensing layers can develop applications of electro-optically modulated SPR, such as sensing drug concentration, sensing affinity of drug and serum albumin, sensing chemical compositions, sensing environmental contamination, and so on. Objections of the invention are increasing sensitivity of SPR, developing system stability, reducing measurement cost, reducing system bulk, and so on.

The SPR is an optical detecting technology, and has advantages of label-free, a real time analysis, specificity, a high sensitivity, an ability of mass parallel detection, and so on. When the incidence light beam inputs an interface between metal and medium, if the component of wave vector of the incidence light beam is equal to the wave vector of the surface plasma wave, the energy transfer from the incidence light beam occurs such that the surface plasma waves is excited on the interface between metal and medium, which is named as SPR. The SPR can evidently change the intensity and the phase of the output optical wave. Property changes of medium on the metal surface can be sensed by detecting changes of the intensity or the phase of the output optical wave.

Currently, methods for modulating the wave vector of the incidence light beam mainly include two kinds: one is modulating the incidence angle of the incidence light beam, and the other is modulating the wavelength of the incidence light beam. The method of modulating the incidence angle of the input light beam utilizes a mechanical device to rotate a prism, and the detection resolution is limited by the resolution and the stability of the mechanical device rotation. Furthermore, the mechanical device has a huge bulk, and is hardly moved and arranged. The method of modulating the wavelength of the incidence light beam utilizes a stable broadband light source and a high resolution spectrometer to detect the spectrum change of the output light beam. The method of modulating the wavelength of the incidence light beam has a high equipment cost and requires a high environmental stability, and therefore, the method is hardly used in outdoors detection.

In TW patent no. I273231, inventors of the present invention provided a method for modulating the wave vector of incidence light beam using the electro-optical effect, which can detect the property changes of medium on metal surface by measuring the slope of a regression straight line of the relation between the intensity of the output light beam and the applied voltage. The method using the electro-optically modulated SPR can reduce interferences from outer noises, system bulk, and system cost. However, because environmental noises heavily interfere the detection of the intensity of optical wave, the detection resolution can not be further improved. Moreover, the phase shift caused by the SPR will acutely changes with the property changes of an under-testing object.

What is needed is a testing method for using electro-optically modulated surface plasmon resonance based on phase detection, which can effectively reduce noises, and improve a detection sensitivity and a detection resolution.

BRIEF SUMMARY

The present invention provides a method and a device for detecting the property of an object using electro-optically modulated surface plasmon resonance (SPR) based on phase detection. The operation principle is applying a voltage on a sensing element made of an electro-optic crystal to modulate the wave vector of input light beam by electro-optic effect, and then, measuring the relation between the phase of output optical wave of the sensing device and the applied voltage, and the property changes of an under-testing object can be obtained by the slope of a regression line of this relation.

Because the phase detection of optical wave can be less interfered by environmental noises, and phase shift caused by the SPR will acutely changes with the property changes of an under-testing object, the present invention provides a method of utilizing electro-optic effect to modulate wave vector of input light beam, and designs a phase detecting structure of SPR to perform phase detection of electro-optically modulated SPR. The present invention can effectively reduce noises, and improve the detection sensitivity and the detection resolution. The present invention can be utilized in an attenuated-total-reflection (ATR) structure and an optical waveguide structure, which are two kinds of structures currently used most commonly in SPR detection.

The following takes an example of the SPR device of Kretschmann configuration in an ATR structure to illustrate the detection process of measuring the phase shift varied with the applied voltage to determine the property of an under-testing object. FIG. 1 shows a SPR device of Kretschmann configuration in an ATR structure. The SPR device includes a first medium (prism) 11, a second medium (metal medium) 12, and a third medium (under-testing object) 13. The first medium 11 has a refractive index of $n_1$, and the third medium 13 has a refractive index of $n_3$. The second medium has a refractive index of $n_2$ and a thickness of d2, wherein the $n_2$ is satisfied with $n_2 = n + i \cdot k$.

In the detection process, a linearly polarized light inputs the second medium 12 from the first medium 11 with an incidence angle θ. When the incidence angle θ is chosen such that the component of the wave vector of the input light along the direction of an interface is equal to the wave vector of the surface plasma wave, the surface plasma wave will be excited on an interface between the second medium 12 and the third medium 13. When the optical wave input the three-layer structure, the reflection coefficients of the TM-polarized light and the TE-polarized light can be denoted as following:

$$r_q = \frac{r_{1,2}^q + r_{2,3}^q e^{i2k_{z2}d_2}}{1 + r_{1,2}^q r_{2,3}^q e^{i2k_{z2}d}} = |r_q| e^{i\phi_q} \quad (1)$$

$$q = TM, TE$$

Wherein the $k_{zi}$ is the wave vector of an incidence light transmitting in a medium i along a direction z (parallel to the interface direction). The $r_{ij}^{TM}$ and $r_{ij}^{TE}$ denote Fresnel reflection coefficients of the TM-polarized light and the TE-polarized light, which are inputted from a medium i to the medium j, respectively. They can be denoted as following:

$$r_{i\,j}^{TM} = \frac{k_{zi} - k_{zj}}{k_{zi} + k_{zj}} \quad (2)$$

$$i, j = 1, 2, 3$$

$$r_{i\,j}^{TE} = \frac{n_j^2 k_{zi} - n_i^2 k_{zj}}{n_j^2 k_{zi} + n_a^2 k_{zj}} \quad (3)$$

$$i, j = 1, 2, 3$$

$$k_{zi} = k_0(n_i^2 - n_1^2\sin^2\theta)^{1/2} \quad (4)$$

Wherein the $k_0$ is the wave vector in the vacuum. Under the conditions of SPR, a phase shift between the TM-polarized light and the TE-polarized light reflected and returned from the surface side can be denoted as following:

$$\phi = \phi_{TM} - \phi_{TE} \quad (5)$$

Referring to formulas (1), (2) and (3), the phase shift $\phi$ is related to the refractive index $n_1$ and the refractive index $n_3$. The refractive index $n_1$ of the first medium 11 can be electro-optically modulated by applying a voltage, and therefore, the phase shift $\phi$ is a function of the voltage and the refractive index $n_3$ of the third medium 13. According to the principle in calculus, the differential of the phase shift function with respect to the applied voltage is also a function of $n_3$. This differential function value can be approximated by using the slope of the regression line of the relation between the phase shift of the output optical wave and the applied voltage, and therefore, the property changes of the third medium 13 can be detected by measuring the slope of the regression line of the relation between the phase of the output optical wave and the voltage. Furthermore, the phase shift produced by electro-optically modulated SPR can be transferred into the optical intensity change by an interference manner, and consequently, the step of measuring the relation between the phase of the output optical wave and the applied voltage is changed into measuring relation between the optical intensity of the output optical wave and the applied voltage.

The third medium 13 can be an under-testing liquid/film or a biochemical sensing layer according to the application of the sensing elements. Properties of the under-testing object include the refractive index of the under-testing liquid/film, the concentration or interactions of the biochemical molecules. Optical wavelengths used in detection can be selected according to the under-testing object type. Because the sensitivity of sensing element is dependent on the optical wavelength, the wavelength with the best sensitivity will be selected. When the electro-optically modulated surface plasmon resonance (SPR) based on phase detection is utilized to an optical waveguide structure, the first medium is changed into a waveguide layer, and the other two mediums are not changed. The incidence light is transmitted in the optical waveguide, and the surface plasma wave is excited on the metal layer on the waveguide surface.

In the following embodiments, a biochemical sensing layer to be used is a human serum albumin manufactured by a self-assembly technology, and an under-testing liquid is a beta-blocker solution. The beta-blocker is a drug for curing heart disease. The biochemical sensing layer can be utilized to detect the concentration of the beta-blocker in the solution and the interaction affinity of the beta-blocker and the human serum albumin. The metal layer utilized to excite the surface plasma wave can be a pure gold film, a pure silver film or other metal film, or be nanometer particles of a single metal, such as gold nanoparticles, silver nanoparticles, or nanoparticles made of at least two kinds of metal material, or be nanoparticles and a metal film with each other. Because the phenomena of surface plasmon resonance are dependent on the dielectric coefficients of metal, sizes, forms, and distributions of the nanoparticles, the detection sensitivity will be clearly affected by these parameters.

The present invention provides the technique of the electro-optically modulated SPR based on phase detection, which utilizes the electro-optic effect to modulate the refractive index of an electro-optic crystal, and further to modulate the wave vector of the incidence optical wave, and then, uses measuring the slope of a regression straight line of the relation between the phase shift of the output light and the applied voltage to detect the properties of an under-testing object. Because phase detection of optical wave can be less interfered by environmental noises, the present invention can effectively reduce noises during measuring. Furthermore, the present invention provides a method of measuring the relation between the phase shift and the applied voltage, which belongs to relative phase measurement. Not only the noise can be further reduced by using a regression straight line analysis, but also there is no need of measuring the absolute phase values. Therefore, the present invention can effectively reduce the cost of measurement equipments and the fee for calibration of absolute phase measurement. In addition, because the present invention uses electrical signals during detection, comparing with conventional mechanical modulating incidence angles and wavelengths, the present invention has advantages of high resolution, short detection time, no need of calibration of absolute phase measurement, and a low equipment cost.

The first embodiment of the present invention is a device for detecting an analyte using electro-optically modulated SPR based on phase detection, which uses inputting optical wave to the device to produce the SPR, and detecting an under-testing object according to the relation between the phase shift and the applied voltage. The device includes two kinds of structures: one is an ATR structure shown in FIG. 2, and the other is an optical waveguide structure shown in FIG. 3.

The ATR structure shown in FIG. 2 includes a light incidence medium, a first medium (electro-optic crystal) arranged under the light incidence medium, and a second medium (layer for producing surface plasma wave) arranged under the first medium. An index matching liquid is covered on the interface between the light incidence medium and the first medium to reduce reflections from the interface. A voltage is applied on the electrode to produce the electric field in the first medium to change its refractive index. An electrode portion is arranged on the bottom of the first medium, and an insulation layer is covered on the electrode portion to prevent the electrode portion from short circuit. The layer for producing surface plasma wave can be a metal layer, and a biochemical sensing layer can be added under the layer for producing surface plasma wave to detect biochemical molecule reactions. Consequently, when arranging an under-testing object under the second medium, an input optical wave from the light incidence medium passes through the first medium and input the metal layer, and then applying a voltage on the electrode portion and measuring the relation between the phase shift of the output optical wave and the applied voltage to determine a concentration or a property of the under-testing object.

The device in the optical waveguide structure shown in FIG. 3 uses inputting optical wave to optical waveguides to produce the SPR, and detecting an under-testing object according to the relation between the phase shift and the applied voltage. The device in the optical waveguide structure includes a first medium, a waveguide arranged as the first medium, the waveguide having a detection area; a second medium, taken as a layer for producing surface plasma wave, arranged on the detection area; arranging an under-testing object over the second medium; two electrodes, arranged on the two sides of the detection area respectively, and being capable of producing an electrical field in an electro-optic crystal substrate by applying a voltage and thus modulating the refractive index of the optical waveguide, as shown in FIG. 3. By putting the under-testing object over the second medium, the concentration or the material property of the under-testing object can be determined by inputting an optical wave into the waveguide, and measuring the relation between the phase shift of the output optical wave and the applied voltage.

A second embodiment of the present invention is a method for detecting an object using electro-optically modulated surface plasmon resonance (SPR) based on phase detection, which is inputting optical wave to sensing devices, when the component of wave vector of incidence optical wave is equal to the wave vector of surface plasma waves, energy of the incidence optical wave will be transferred to the surface plasma wave to make the SPR occur, at this time, intensity and phase of an output optical wave will be changed. The present invention uses applying a voltage on an electro-optic crystal to modulate the characters of the SPR by electro-optic effect, and causes the phase of the output optical wave being modulated by the voltage. Relations between the phase of the output optical wave and the voltage are related to the property of the under-testing object, and therefore, the present invention can be utilized to detect the property of the under-testing object. The method includes: (1) inputting optical wave to an electro-optically modulated SPR sensing device; (2) applying a voltage on the electro-optically modulated SPR sensing device to produce an electrical field in an electro-optic crystal of the electro-optically modulated SPR sensing device to modulate the surface plasmon resonance condition; (3) measuring the relation between the phase shift of output optical wave and the applied voltage from the electro-optically modulated SPR sensing device; (4) using the linearity regression analysis to compute the slope of the regression straight line of the relation between the phase of output optical wave and the applied voltage; (5) using calibration data of relations between the slope of the regression straight line and the concentration (or the material property) of a standard solution (or a standard material) to compute the concentration (or the material property) corresponding to the measured slope of the regression straight line, wherein the concentration (or the material property) of the object is determined by the concentration (or the material property) corresponding to the measured slope of the regression straight line.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
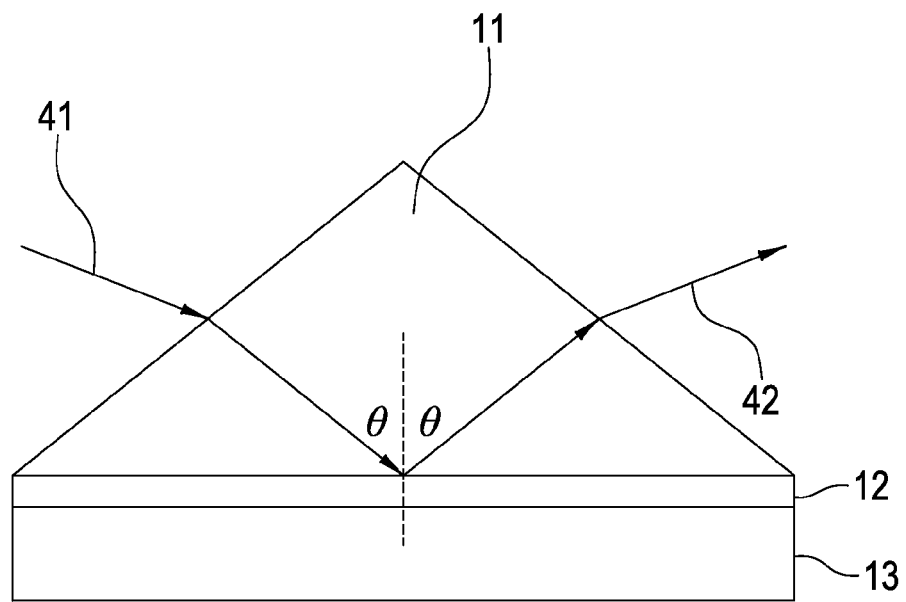
FIG. 1 shows a surface plasmon resonance (SPR) device of Kretschmann configuration in an attenuated-total-reflection (ATR) structure.
Figure 2:
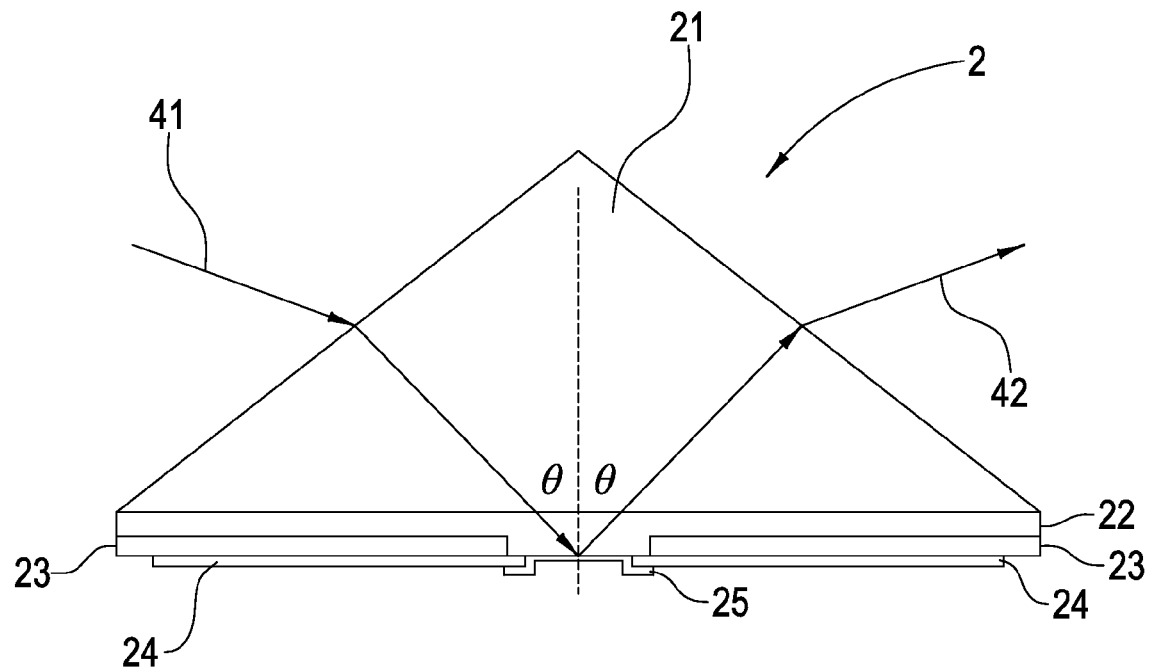
FIG. 2 is a schematic view of a SPR device used in an ATR structure of an electro-optically modulated SPR based on phase detection.
Figure 3:
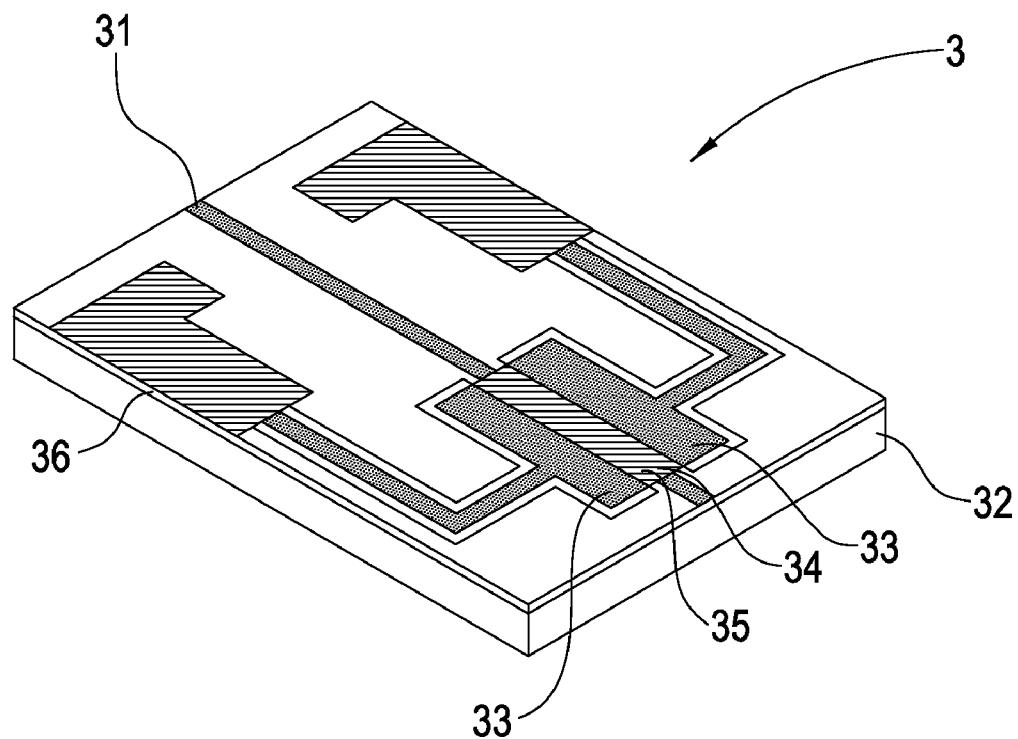
FIG. 3 is a schematic view of a SPR element used in an optical waveguide structure of an electro-optically modulated SPR based on phase detection.

Embodiments of the present invention providing a device for detecting an object using electro-optically modulated surface plasmon resonance (SPR) based on phase detection includes the Kretschmann configuration of an attenuated-total-reflection (ATR) structure 2 shown in FIG. 2, and an optical waveguide structure 3 shown in FIG. 3. FIG. 2 shows a SPR device used in an ATR structure of an electro-optically modulated SPR based on phase detection. The ATR structure 2 includes a light incidence medium 21, a first medium 22 (electro-optic crystal) arranged under the light incidence medium 21, and a second medium 25 (layer for producing surface plasma wave) arranged under the first medium 22. An index matching liquid is covered on the interface between the light incidence medium 21 and the first medium 22 to reduce the reflection on the interface. A pair of electrodes 23 are arranged on the first medium 22 opposite to an interface between the first medium 22 and the light incidence medium 21, and the pair of electrodes 23 are taken as a portion for applying a voltage. To prevent short circuit, an insulation layer 24 is covered on the electrodes 23, and the insulation layer 24 can be made of silicon oxide or other insulation material. The center of the insulation layer 24 is a detection area, and the second medium 25 is arranged on the detection area and taken as a layer for producing surface plasma wave. The layer for producing the surface plasma wave can be a film of gold, silver or other metal capable of exciting the surface plasma wave, or metal nanoparticles. A film of a human serum albumin manufactured by the self-assembly technology is taken as a biochemical sensing layer is arranged on the surface of the layer for producing surface plasma wave to detect the concentration of a beta-blocker solution. When a voltage is applied on the electrodes 23, the electric field is produced to modulate refractive index of the first medium 22, and further to change the wave vector of incidence optical wave, and then to modulate the phase of output optical wave. When using the ATR structure 2 to detect an under-testing object (not labeled), the under-testing object is arranged under the second medium 25, and is taken as the third medium. Using the operation principle of the SPR device of Kretschmann configuration of the ATR structure shown in FIG. 1 can detect the material property of the under-testing object.

Figure 4:
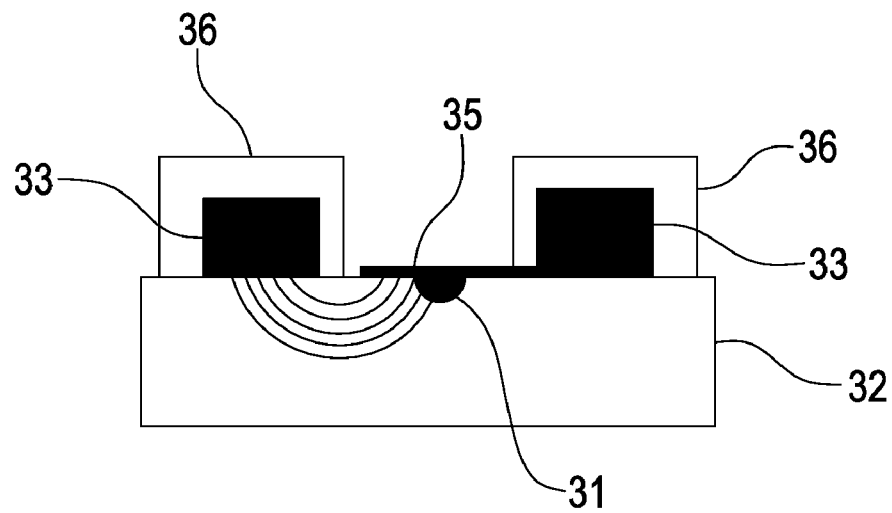
FIG. 4 is a schematic, cross-sectional view of the detection area in the SPR element with the optical waveguide structure capable of using an electro-optically modulated SPR based on phase detection.

FIG. 3 is a schematic view of a SPR element used in an optical waveguide structure of the electro-optically modulated SPR based on phase detection. FIG. 4 is a schematic, cross-sectional view of the detection area of the SPR element of the optical waveguide structure capable of using an electro-optically modulated SPR technology based on phase detection. The SPR element is formed on a first medium 32 (an electro-optic substrate, such as, lithium niobate). The SPR element includes a waveguide 31 (titanium diffused waveguide or other types of waveguides by introducing other ions), a second medium 35 (a layer for producing surface plasma wave), a pair of electrodes 33, and an insulation layer 36 (silicon oxide). The second medium 35 is a layer for producing surface plasma wave, which can be a film of gold, silver, or other metal capable of exciting the surface plasma, or metal nanoparticles. The waveguide 31 has a port for an incidence light entrance, and a detection area 34. The second medium 35 is formed on the detection area 34. The electrodes 33 are arranged on the two sides of the detection area 34. The second medium 35 connects with one of the electrodes 33 for using the largest electro-optical coefficient $r_{33}$ of the lithium niobate electro-optic crystal. In order to limit the influence of the under-testing liquid on the optical field transmitting in the detecting area 34, the insulation layer 36 is arranged on the first medium 32, and the insulation layer 36 has an opening corresponding to the detection area 34.

A cross-sectional view of the detection area 34 when applying a voltage thereto is shown in FIG. 4. When a voltage is applied on the electrodes in the detection area 34, the SPR element will produce the electric field in the waveguide 31. Refractive index of the waveguide 31 will change with the voltage by electro-optic effect, and further, the wave vector of incidence optical wave will be changed, so that the object of modulating the phase of SPR is obtained. The insulation layer 36 are arranged on the electrodes 33 to insulate the electrodes 33 and the under-testing liquid, in order that the under-testing liquid will not result in the short circuit of the electrodes 33 when the voltage is applied. In order to excite the surface plasma wave, the second medium 35 is arranged on the detection area 34, and accordingly, optical wave transmitting in the waveguide 31 can produce the surface plasma wave in the second medium 35 to perform the detection. When using the SPR element to detect an under-testing object (not labeled), the under-testing object is arranged on the second medium 25, and is taken as the third medium. Using the same operation principle of the SPR device of Kretschmann configuration of the ATR structure shown in FIG. 1 can detect the material property of the under-testing object.

Figure 5:
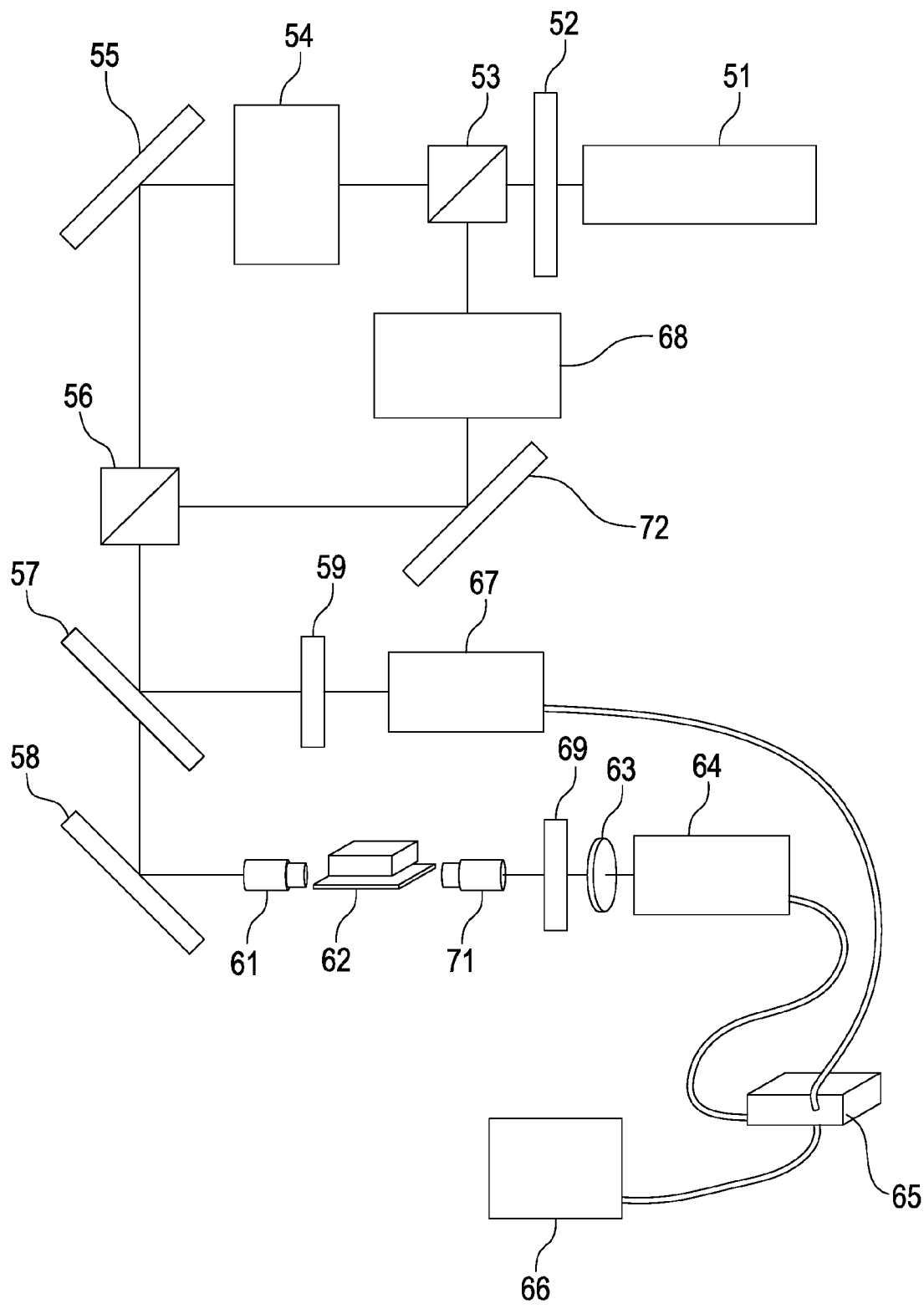
FIG. 5 shows an experimental arrangement for measuring phase of the optical waveguide structure by the electro-optically modulated SPR.

FIG. 5 shows an experimental arrangement of measuring phase of the SPR element of the optical waveguide structure for the electro-optically modulated SPR. The experimental arrangement uses a heterodyne laser light, which is acousto-optically modulated, or is electro-optically modulated. The following will illustrate the experimental arrangement. Firstly, the light from a frequency-stabilized He—Ne laser 51 passes through a half-wave plate 52 and a first polarization splitter 53 to output two light beams with different polarizations. And then, the two vertical polarizing light beams input an acousto-optic modulator 54 and an acousto-optical modulator 68 respectively, and thereby, the two vertical polarizing light beams have the frequency difference. Then after, the two vertical polarizing light beams are reflected by a mirror 55 and a mirror 72 respectively to a second polarization splitter 56 to be combined with each other, so that, the heterodyne laser light is obtained. When measuring, a beam splitter 57 split two partial light beams, and one of the partial light beams passes through a polarizer 59 arranged at an angle of 45° to produce interference, and then is received by an optical detector 67 to produce a reference electrical signal. The other portion of the heterodyne laser light is reflected by a mirror 58, and are focused by a microscope objective 61 to input into the sensing element 62. The sensing element 62 is the structure disclosed in FIG. 2 or FIG. 3. Light beam output from the sensing element 62 is focused by a microscope objective 71, and then to pass through a polarizer 69 and a pinhole 63, then after, is received by an optical detector 64 to produce a measuring electrical signal. In the waveguide structure of the sensing element, if the elements are coupled with fibers at input and output ports, the microscope objective can be canceled. The reference electrical signal and the measuring electrical signal are input into a lock-in-amplifier 65 to measure the phase shift between them. During measuring the phase shift, firstly changing the applied voltage, and then reading the phase shift value using a computer 66, and then after measuring the phase relation between the reference electrical signal and the measuring electrical signal, the computer automatically compute the slope of a regression straight line of the relations.

Figure 6:
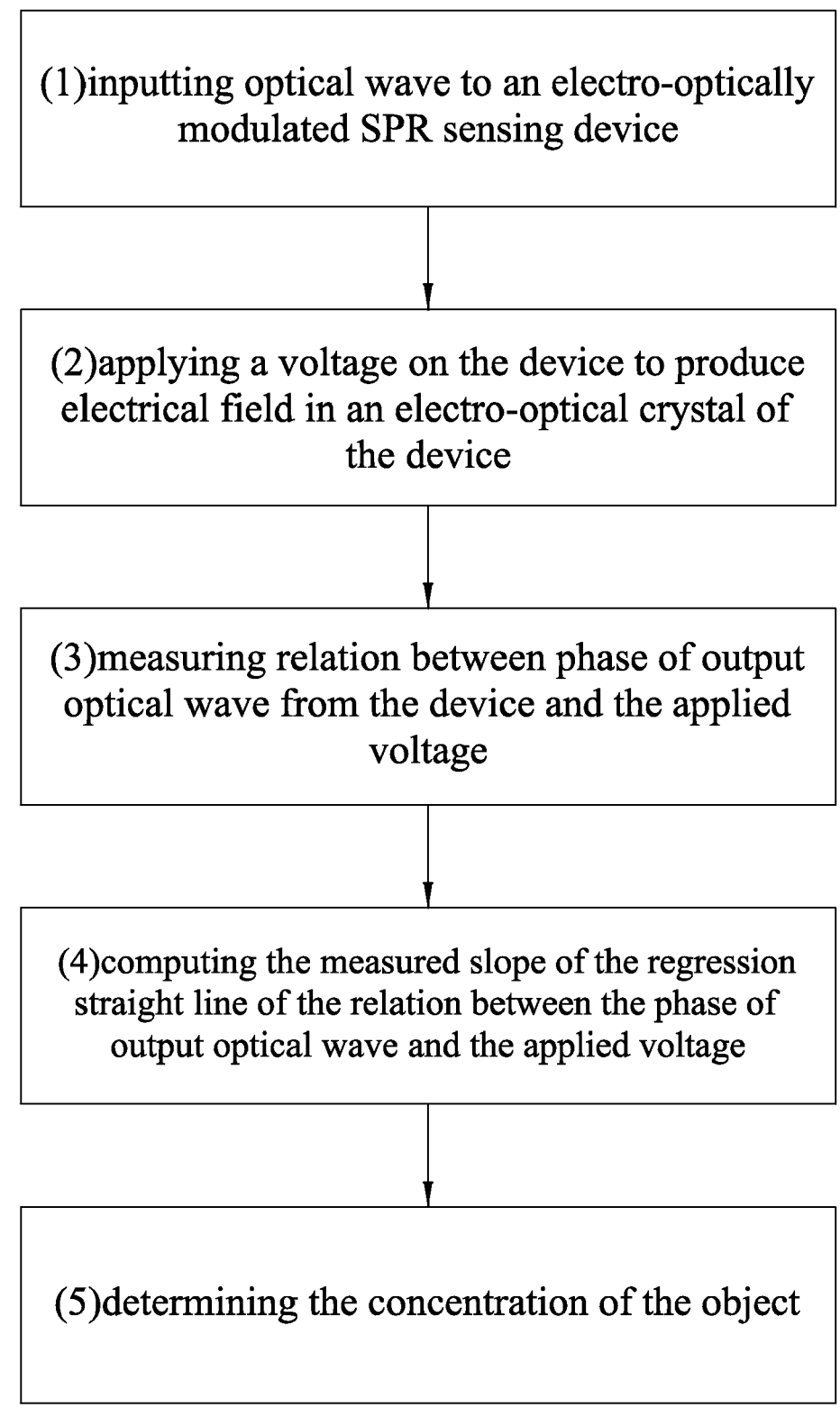
FIG. 6 is a flow chart of a method for detecting an object using electro-optically modulated SPR based on phase detection.

FIG. 6 is a flow chart of a method for detecting an object using electro-optically modulated SPR based on phase detection. The method uses inputting optical wave to a detecting device to produce the SPR, and detect according to the relation between the phase of output optical wave and the applied voltage. The method includes the following steps:
(1) inputting optical wave to an electro-optically modulated SPR sensing device;
(2) applying a voltage to the electrodes of the electro-optically modulated SPR sensing device to produce the electrical field in an electro-optic crystal of the electro-optically modulated SPR sensing device;
(3) measuring the relation between the phase of output optical wave, from the electro-optically modulated SPR sensing device, and the applied voltage;
(4) using the linearity regression analysis to compute the slope of a regression straight line of the relation between the phase of output optical wave and the voltage in the step (3);
(5) using calibration data of relation between the slope of the regression straight line and the concentration (or a material property) of a standard solution (or a standard material) to compute the concentration (or the material property) corresponding to the measured slope of the regression straight line, wherein the concentration (or the material property) of the object is determined by the concentration (or the material property) corresponding to the measured slope of the regression straight line.

Figure 7:
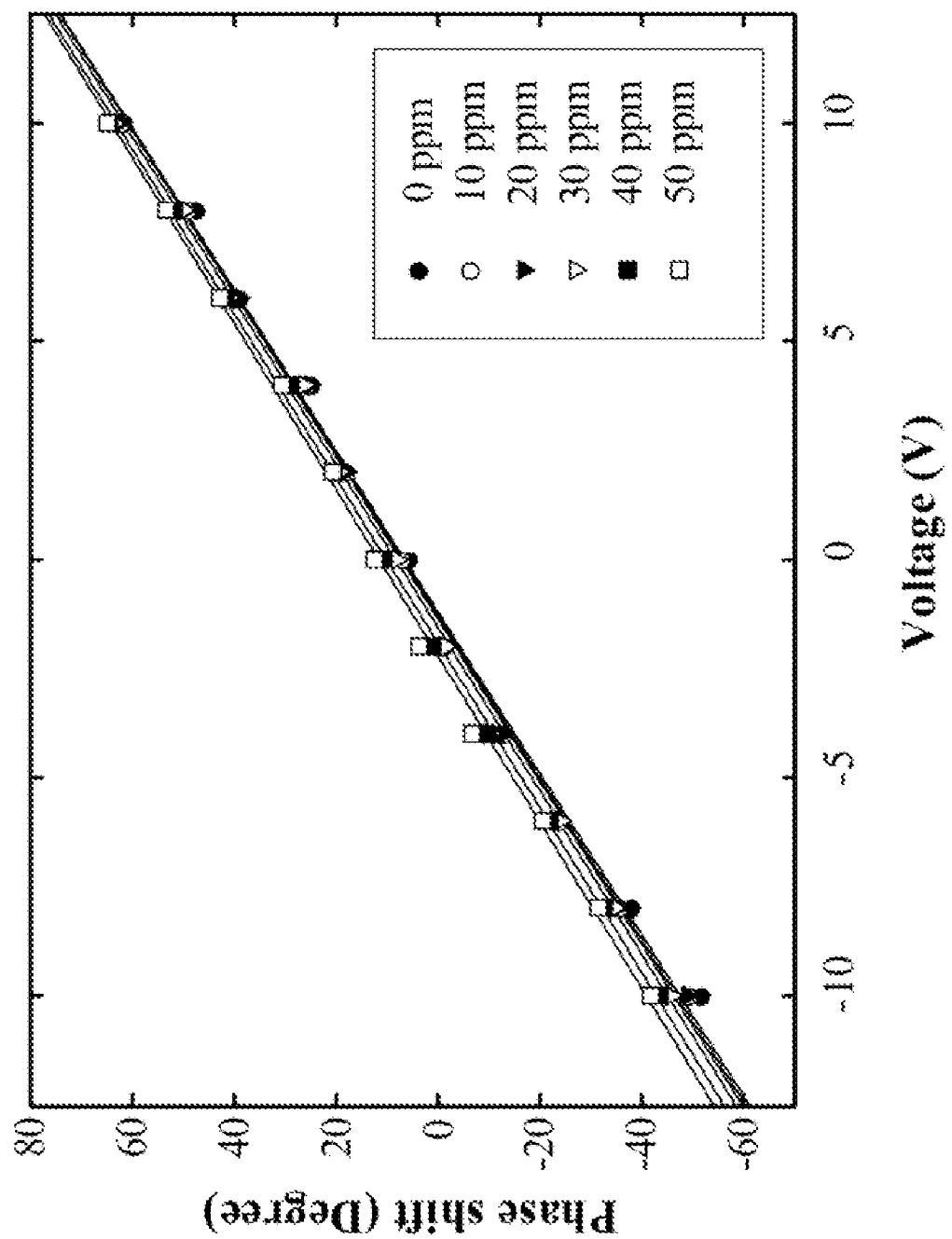
FIG. 7 shows the relation between the phase shift of output optical wave and the applied voltage for various concentrations of beta-blocker solutions.
Figure 8:
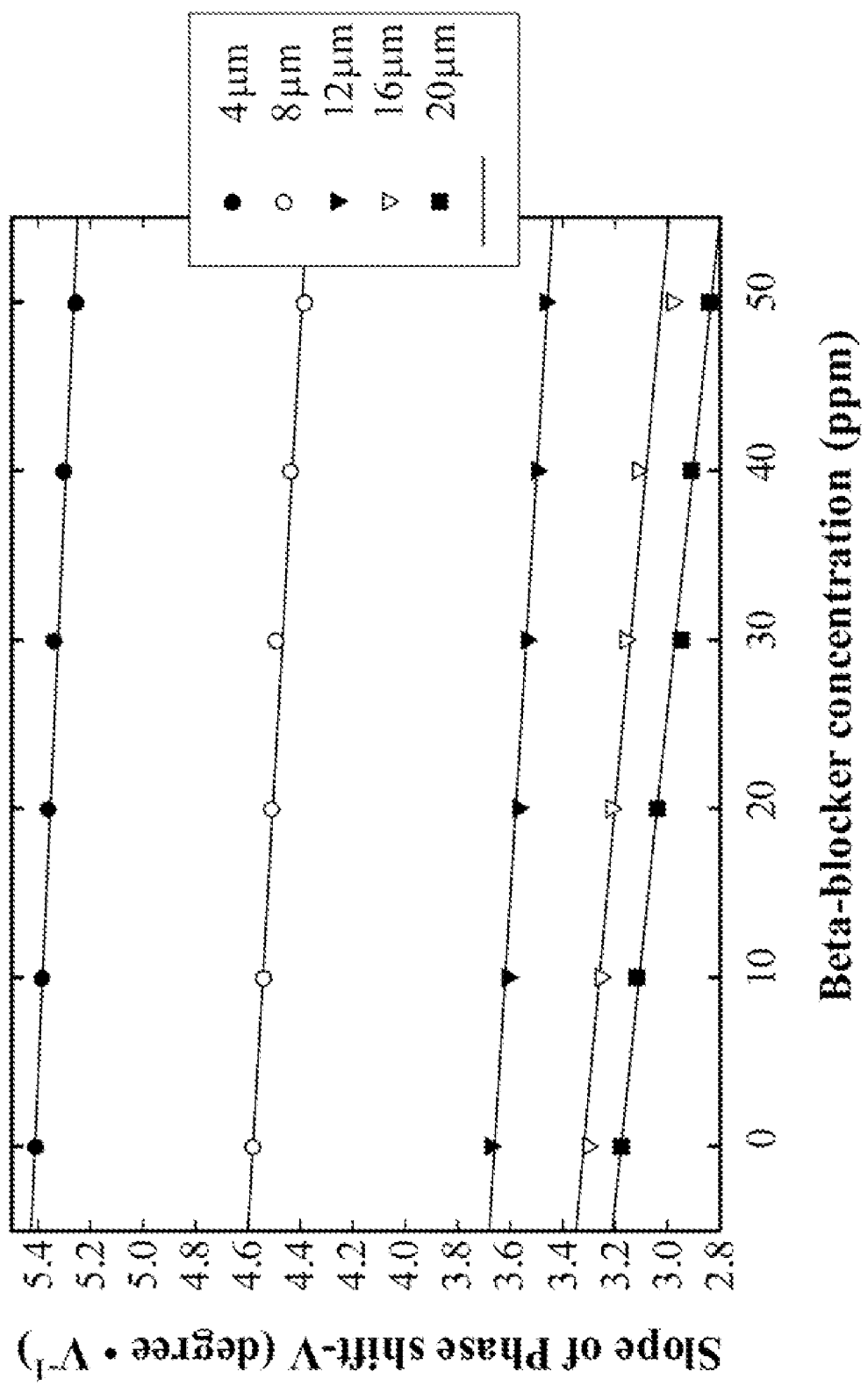
FIG. 8 shows the dependence of slope of a regression straight line of the relation between the phase shift and the applied voltage on the concentration of the beta-blocker solution for SPR sensing devices with various waveguide widths.

FIG. 7 shows the dependence of phase shift of output optical wave on the applied voltage for various beta-blocker solutions. When the applied voltage is increased, the phase shift will be increased, and the phase shift and the applied voltage have a linear relation. FIG. 8 shows the dependence of the slope of the regression straight line of the relation between the phase shift and the applied voltage on the concentration of the beta-blocker solution according to SPR sensing devices with various waveguide widths, such as 4 μm, 8 μm, 12 μm, 16 μm, 20 μm. As shown in FIG. 8, when the concentration of the beta-blocker is higher, the slope of the regression straight line is smaller. Therefore, the concentration of the beta-blocker is detected by measuring the slope of the regression straight line of the relation between the phase shift and the applied voltage.

The above description is given by way of example, and not limitation. Given the above disclosure, one skilled in the art could devise variations that are within the scope and spirit of the invention disclosed herein, including configurations ways of the recessed portions and materials and/or designs of the attaching structures. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method for detecting object properties using electro-optically modulated surface plasmon resonance (SPR) based on phase detection, the method comprising:
inputting optical wave to an electro-optically modulated SPR sensing device;
applying a voltage on the electro-optically modulated SPR sensing device to produce electrical field in an electro-optical crystal of the electro-optically modulated SPR sensing device;
measuring relation between phase of output optical wave from the electro-optically modulated SPR sensing device and the applied voltage;
using linearity regression analysis to compute measured slope of the regression straight line of the relation between the phase of output optical wave and the applied voltage;
using calibration data of the relation between the slope of the regression straight line and concentration or material property of a standard solution or a standard material to compute concentration or material property corresponding to the measured slope of the regression straight line, wherein the concentration or the material property of the object is determined by the concentration or the material property corresponding to the measured slope of the regression straight line.

2. The method for detecting object properties using electro-optically modulated SPR based on phase detection of claim 1, wherein phase shift produced by the electro-optically modulated SPR is able to be transferred into light intensity change by an interference manner, and the step of measuring the relation between the phase of output optical wave and the applied voltage is changed into measuring the relation between the intensity of the output optical wave and the applied voltage.

3. A device for detecting object properties using electro-optically modulated surface plasmon resonance (SPR) based on phase detection, the device belonging to a SPR device of attenuated-total-reflection structure, the device comprising:
a first medium;
a second medium, taken as a layer for producing surface plasma wave, arranged under the first medium;
an electrode portion, utilized to produce the electrical field on the first medium to modulate refractive index of first medium by applying a voltage;
arranging an under-testing object under the second medium, wherein inputting an input optical wave into the first medium, and measuring the relation between the phase shift of the output optical wave and the applied voltage to determine the concentration or the material property of the under-testing object.

4. The device for detecting object properties using electro-optically modulated SPR based on phase detection of claim 3, wherein the first medium is a substrate made of material with electro-optic effect, and the second medium is made of metal.

5. The device for detecting object properties using electro-optically modulated SPR based on phase detection of claim 3, wherein the electrode portion is arranged on two sides of the first medium, and an insulation layer is covered on the electrode portion.

6. The device for detecting object properties using electro-optically modulated SPR based on phase detection of claim 4, wherein the layer for producing surface plasma wave is metal film or metal nanoparticles of gold, silver, or other metal material capable of exciting the surface plasma wave.

7. The device for detecting object properties using electro-optically modulated SPR based on phase detection of claim 5, wherein material of the insulation layer is silicon oxide or other insulating material capable of protecting the electrode portion from short circuit.

8. The device for detecting object properties using electro-optically modulated SPR based on phase detection of claim 3, wherein a light incidence medium is put near the first medium on opposite side of an interface between the first medium and the second medium.

9. The device for detecting object properties using electro-optically modulated SPR based on phase detection of claim 4, wherein the light incidence medium is a prism.

10. A device for detecting object properties using electro-optically modulated surface plasmon resonance (SPR) based on phase detection, the device belonging to a SPR device of optical waveguide structure, the device comprising:
a first medium, a waveguide arranged as the first medium, the waveguide having a detection area;
two electrodes, arranged on two sides of the detection area respectively, and being capable of producing the electrical field in an electro-optic crystal substrate by applying a voltage;
a second medium, taken as a layer for producing surface plasma wave, arranged on the detection area; arranging an under-testing object over the second medium, wherein inputting the optical wave into the waveguide, and measuring the relation between the phase shift of output optical wave and the applied voltage to determine concentration or material property of the under-testing object.

11. The device for detecting object properties using electro-optically modulated SPR based on phase detection of claim 10, wherein the first medium is made of lithium niobate or other material with electro-optic effect.

12. The device for detecting object properties using electro-optically modulated SPR based on phase detection of claim 10, wherein the waveguide is formed by diffusing titanium or introducing other ions on the first medium.

13. The device for detecting object properties using electro-optically modulated SPR based on phase detection of claim 10, wherein the second medium is metal film or metal nanoparticles of gold, silver, or other metal material capable of exciting the surface plasma wave.

14. The device for detecting object properties using electro-optically modulated SPR based on phase detection of claim 10, wherein an insulation layer is covered on the two electrodes to avoid short circuit.

15. The device for detecting object properties using electro-optically modulated SPR based on phase detection of claim 14, wherein material of the insulation layer is silicon oxide or other insulating material capable of protecting the two electrodes from short circuit.

* * * * *